(12) United States Patent
Deng

(10) Patent No.: US 9,006,441 B2
(45) Date of Patent: Apr. 14, 2015

(54) CONJUGATE ADDITION REACTIONS USING BIFUNCTIONAL CINCHONA-ALKALOID-BASED CATALYSTS

(71) Applicant: Brandeis University, Waltham, MA (US)

(72) Inventor: Li Deng, Newton Lower Falls, MA (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 14/274,028

(22) Filed: May 9, 2014

(65) Prior Publication Data

US 2014/0249313 A1 Sep. 4, 2014

Related U.S. Application Data

(62) Division of application No. 13/133,438, filed as application No. PCT/US2009/066990 on Dec. 7, 2009, now Pat. No. 8,722,891.

(60) Provisional application No. 61/120,612, filed on Dec. 8, 2008.

(51) Int. Cl.
*C07D 453/04* (2006.01)
*C07C 67/313* (2006.01)
*C07C 253/30* (2006.01)
*C07D 207/327* (2006.01)

(52) U.S. Cl.
CPC ............ *C07D 453/04* (2013.01); *C07C 67/313* (2013.01); *C07C 253/30* (2013.01); *C07D 207/327* (2013.01)

(58) Field of Classification Search
USPC ........................................................ 546/134
See application file for complete search history.

(56) References Cited

PUBLICATIONS

Baudequin et al., Green Chemistry (2002), 4(6), pp. 584-586.*

* cited by examiner

*Primary Examiner* — Niloofar Rahmani
(74) *Attorney, Agent, or Firm* — Foley Hoag LLP

(57) ABSTRACT

One aspect of the present invention relates to quinine-based and quinidine-based catalysts. Another aspect of the present invention relates to a method of preparing a chiral, non-racemic compound from a prochiral electron-deficient alkene, comprising the step of: reacting a prochiral electron-deficient alkene with a nucleophile in the presence of a catalyst; thereby producing a chiral, non-racemic compound; wherein said catalyst is a derivatized quinine or quinidine.

17 Claims, 1 Drawing Sheet

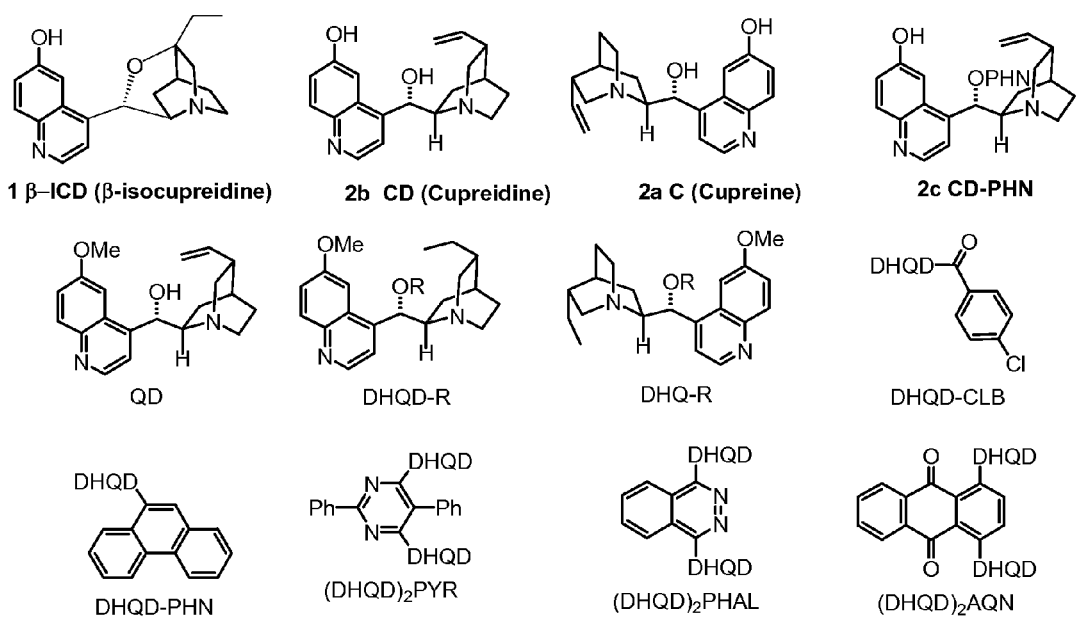

CONJUGATE ADDITION REACTIONS USING BIFUNCTIONAL CINCHONA-ALKALOID-BASED CATALYSTS

RELATED APPLICATIONS

This application is a divisional application of U.S. application Ser. No. 13/133,438, now U.S. Pat. No. 8,722,891, which is a §371 national stage application based on Patent Cooperation Treaty Application serial number PCT/US2009/066990, filed Dec. 7, 2009; which claims the benefit of priority to U.S. Provisional Patent Application Ser. No. 61/120,612, filed Dec. 8, 2008.

GOVERNMENT SUPPORT

The invention was made with support provided by the National Institutes of Health (GM-61591); therefore, the government has certain rights in the invention.

BACKGROUND OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. These advantages include the fewer side effects and greater potency often associated with enantiomerically pure compounds.

Traditional methods of organic synthesis were often optimized for the production of racemic materials. The production of enantiomerically pure material has historically been achieved in one of two ways: use of enantiomerically pure starting materials derived from natural sources (the so-called "chiral pool"); and the resolution of racemic mixtures by classical techniques. Each of these methods has serious drawbacks, however. The chiral pool is limited to compounds found in nature, so only certain structures and configurations are readily available. Resolution of racemates, which requires the use of resolving agents, may be inconvenient and time-consuming.

Enantiomerically pure materials may be obtained by asymmetric conjugate addition of a nucleophile to an electron-poor alkene. The asymmetric conjugate addition is one of the most powerful bond-forming reactions to construct enantioenriched, highly functional carbon skeletons for the total synthesis of natural and biologically active compounds. For reviews see: (a) B. E. Rossiter, N. M. Swingle, *Chem. Rev.* 1992, 771-806; (b) J. Leonard, E. Diez-Barra, S. Merino, *Eur. J. Org. Chem.* 1998, 2051-2061; (c) K. Tomioka, Y Nagaoka, *Comprehensive Asymmetric Catalysis* (Eds.: E. N. Jacobsen, A Pfaltz, H. Yamamoto), Springer, Berlin, 1999, vol. 3, p. 1105-1120; (d) M. Yamaguci, *Comprehensive Asymmetric Catalysis* (Eds.: E. N. Jacobsen, A Pfaltz, H. Yamamoto), Springer, Berlin, 1999, vol. 3, p. 1121-1139; (e) M. P. Sibi, S. Manyem, *Tetrahedron* 2000, 56, 8033-8061; (f) N. Krause, A. Hoffmann-Roder *Synthesis* 2001, 171-196. For general reviews on conjugate additions see: (g) P Perlmutter, *Conjugate Addition Reactions in Organic Synthesis* (Eds.: J. E. Baldwin, P D. Magnus), Pergamon Press, Oxford, 1992; (h) M. E. Jung, *Comprehensive Organic Synthesis* (Ed.: B. M. Trost), Pergamon Press, Oxford, 1991, vol. 4, pp. 1-67. Its strategic importance is evident by considering that a Michael addition can represent the initiating step of more complex inter- and intramolecular tandem processes. For reviews see: (a) L. F Tietze, *Chem. Rev.* 1996, 96, 115-136; (b) R. A. Brunce, *Tetrahedron* 1995, 48, 13103-13159; (c) L. Tietze, U. Beifuss, *Angew. Chem.* 1993, 105, 137-170; *Angew Chem. Int. Ed Engl.* 1993, 32, 131-163; (d) G. H. Posner, *Chem. Rev.* 1986, 86, 831-844.

Among the Michael acceptors, nitroalkenes are very attractive, because the nitro group is the most electron-withdrawing group known. N. Ono, *The Nitro Group in Organic Synthesis*, Wiley-VCH, New York, 2001; D. Seebach, E. W. Colvin, F Lehr, T Weller, *Chimia* 1979, 33, 1-18. Often described as a "synthetic chameleon," the nitro group can serve as masked functionality to be further transformed after the addition has taken place. G. Calderari, D. Seebach, *Helv. Chim. Acta* 1995, 68, 1592-1604. The Nef reaction, the nucleophilic displacement, the reduction to amino group, the Myer reaction, and the conversion into a nitrile oxide are only examples of the transformations that nitro groups can undergo. H. W Pinnick, *Org. React.* 1990, 38, 655-792; J. U. Nef, *Justus Liebigs Ann. Chem.* 1894, 280, 263-291; R. Tamura, A. Kamimura, N. Ono, *Synthesis* 1991, 423-434; R. C. Larock, *Comprehensive Organic Transformations*, VCH, New York, 1989, pp. 411-415; A. K. Beck, D. Seebach, *Chem. Ber.* 1991, 124, 2897-2911; R. E. Maeri, J. Heinzer, D. Seebach, *Liebigs Ann.* 1995, 1193-1215; M. A. Poupart, G. Fazal, S. Goulet, L. T Mar, *J. Org. Chem.* 1999, 64, 1356-1361; A. G. M. Barrett, C. D. Spilling, *Tetrahedron Lett.* 1988, 29, 5733-5734; D. H. Lloyd, D. E. Nichols, *J. Org. Chem.* 1986, 51, 4294-4298; V. Meyer, C. Wurster, *Ber. Dtsch. Chem. Ges.* 1873, 6, 1168-1172; M. J. Kamlet, L. A. Kaplan, J. C. Dacons, *J Org. Chem.* 1961, 26, 4371-4375; T. Mukayama, T Hoshino, *J. Am. Chem. Soc.* 1960, 82, 5339-5342. A number of catalytic synthetic methods have been developed in recent years, making use of nitroalkenes even more attractive. A. G. M. Barret, G. G. Graboski, *Chem. Rev.* 1986, 86, 751-762; R. Ballini, R. Castagnani, M. Petrini, *J. Org. Chem.* 1992, 57, 2160-2162; G. Rosini, R. Ballini, M. Petrini, P Sorrenti, *Synthesis* 1985, 515-517.

Conjugate additions of carbon nucleophiles to alkenyl sulfones in parallel to those to nitroalkenes constitute a class of synthetically valuable C—C bond forming reactions. Accordingly, considerable efforts have been devoted to the development of asymmetric conjugate additions to alkenyl sulfones. Although significant advancements have been made in the use of chiral auxiliary strategy, the realization of a highly enantioselective catalytic conjugate additions with alkenyl sulfones remains elusive. For reviews of enantioselective conjugate additions, see (a) Sibi, M. P.; Manyem, S. *Tetrahedron* 2000, 56, 8033-8061; (b) Krause, N.; Hoffmann-Roder, A. *Synthesis* 2001, 171-196; (c) M. Yamaguchi in Comprehensive Asymmetric Catalysis (Eds.: E. N. Jacobsen, A. Pfaltz, H. Yamamoto), Springer, Heidelberg, 2003, Suppl. 1, Supplement to chap. 31.2, p. 151. (a) Pinheiro, S.; Guingant, A.; Desmaële, D.; d'Angelo, J. *Tetrahedron: Asymmetry* 1992, 3, 1003; (b) d'Angelo, J.; Revial, G. *Tetrahedron: Asymmetry* 1991, 2, 199. Lin, Y.; Ali, B. E.; Alper, H. *J. Am. Chem. Soc.* 2001, 123, 7719. For a conjugate addition of chiral 1-aminopyrrolidine to alkenyl sulfones see: Enders, D.; Müller, S. F.; Raabe, G.; Runsink, J. *Eur. J. Org. Chem.* 2000, 879. (a) Reddick, J. J.; Cheng, J.; Roush, W. R. *Org. Lett.* 2003, 5, 1967; (b) Sanki, A. K.; Suresh, C. G.; Falgune, U. D.; Pathak, T. *Org. Lett.* 2003, 5, 1285; (c) Ravindran, B.; Sakthivel, K.; Suresh, C. G.; Pathak, T. *J. Org. Chem.* 2000, 65, 2637; (d) Farthing, C.; Marsden, S. P. *Tetrahedron Lett.* 2000, 41, 4235-4238; (e) Hirama, M.; Hioki, H.; Itô, S.; Kabuto, C. *Tetrahedron Lett.* 1988, 29, 3121. For intramolecular Michael addition to alkenyl sulfones see: Carretero, J. C.; Arrayas, R. G. *J. Org. Chem.* 1998, 63, 2993; for a Rh-catalyzed enantioselective conjugate addition of organoboronic acids to trans-β-substituted vinyl sulfones see: Mauleon, P.; Carretero, J. C. *Org. Lett.* 2004, 6, 3195.

Additionally, the conjugate addition of carbon nucleophiles to alkenyl ketones provides a powerful strategy for the creation of all-carbon quaternary stereocenters, due to the accessibility of a wide range of both the Michael donors and acceptors and the proven wide utility of the 1,4-adducts. Remarkably, in spite of numerous great strides made since then in catalytic asymmetric synthesis, this task remains a daunting challenge of undiminished synthetic significance. Wynberg, H.; Helder, R. *Tetrahedron Letters* 1975, 46, 4057-4060. Sawamura, M.; Hamashima, H.; Ito, Y. *J. Am. Chem. Soc.* 1992, 114, 8295-8296. Sasai, H.; Emori, E.; Arai, T.; Shibasaki, M. *Tetrahedron Letters* 1996, 37, 5561-5564. Hamashima, Y.; Hotta, D.; Sodeoka, M. *J. Am. Chem. Soc.* 2002, 124, 11240-11241. Bella, M.; Jorgensen, A. *J. Am. Chem. Soc.* 2004, 126, 5672-5673. For chiral (salen)Al complex-catalyzed conjugate addition of α-phenyl α-cyanoacetate to an acyclic α,β-unsaturated ketones, see Taylor, M. S.; Zalatan, D. N.; Lerchner, A. M.; Jacobsen, E. N. *J. Am. Chem. Soc.* 2005, 127, 1313-1317. For a special issue focusing on asymmetric catalysis, see: *Proc. Natl. Acad. Sci. USA* 2004, 101, 5347-5850. (b) For a thematic issue for Enantioselective Catalysis see: (Eds: Bolm, C.; Gladysz, J.) *Chem. Rev.* 2003, 103, 2761-3400. (c) *Comprehensive Asymmetric Catalysis*, E. N. Jacobsen, A. Pfaltz, H. Yamamoto Eds, Springer-Verlag, Berlin, 1999, Vol. 1-3. An enantioselective catalytic conjugate addition of α-substituted ketoesters to vinyl ketones was reported by Shibasaki and coworkers in 1994. Sasai, H.; Emori, E.; Arai, T.; Shibasaki, M. *Tetrahedron Letters* 1996, 37, 5561-5564. With a bifunctional chiral La-Na-BINOL complex, the addition of cyclic and acyclic α-substituted ketoesters to methyl vinyl ketone (MVK) proceeded in 62-91% ee. More recently, Sodeoka and coworkers reported a Pd-BINAP complex that afforded 86-93% ee for the conjugate addition of α-substituted ketoesters to methyl and ethyl vinyl ketones. Hamashima, Y.; Hotta, D.; Sodeoka, M. *J. Am. Chem. Soc.* 2002, 124, 11240-11241. These chiral metal complex-mediated reactions, while demonstrating substantial scopes with respect to ketoester donors, afforded greater than 90% ee only with MVK as the Michael acceptor. Moreover, performed at −50 to −20° C., a catalyst loading of 5-10 mol % is required for the reaction to reach completion in 15 to 72 hours. Although representing remarkable progresses, these results underscore both the urgency and challenge for the development of an operationally simple, efficient and rapid enantioselective catalytic conjugate addition of broad substrate scopes for alkenyl ketones.

The present invention relates in part to the catalytic asymmetric synthesis of chiral compounds from prochiral substrates, such as nitroalkenes, alkenyl sulfones and alkenyl ketones.

Catalytic asymmetric synthesis is providing chemists with new and powerful tools for the efficient synthesis of complex molecules. While many of the catalytic systems are metal-based and rely on chiral Lewis acid and organometallic redox-based catalysis, increasing numbers of asymmetric reactions are catalyzed by chiral nucleophiles, building on the vast assortment of situations in nature in which nucleophiles play pivotal roles. For leading references, see: (a) In *Comprehensive Asymmetric Catalysis*; Jacobsen, E. N., Pfaltz, A., Yamamoto, H., Eds.; Springer: Heidelberg, 1999; (b) In *Asymmetric Catalysis in Organic Synthesis*, Noyori, R., Ed.; Wiley: New York, 1994; (c) In *Asymmetric Synthesis*, 2nd ed.; Ojima, I., Ed.; VCH: New York, 2000; (d) Acc. Chem. Res. 2000, 33, 323. (e) Groger, H.; Wilken, J. *Angew. Chem., Int. Ed.* 2001, 40, 529; (f) Pierre, J.-L. *Chem. Soc. Rev.* 2000, 29, 251-257. (g) Roberts, B. P. *Chem. Soc. Rev.* 1999, 28, 25. Chiral amines play a central role in this expanding area of asymmetric catalysis. Although chiral amines have been utilized extensively as chiral ligands, they have also shown great promise in catalyzing a broad range of asymmetric transformations, yielding optically enriched products in high selectivity and yield that may not be accessible through alternative asymmetric technology. Seyden-Penne, J. *Chiral Auxiliaries and Ligands in Asymmetric Synthesis*; Wiley & Sons: New York, 1995.

Historically, the cinchona alkaloids were the first chiral amines to be used in asymmetric catalysis, most notably in the pioneering work of Pracejus from the 1960's on disubstituted ketene alcoholysis. Cinchona alkaloids also possess a rich and colorful history that is rooted in natural products and pharmaceutical chemistry. Turner, R. B.; Woodward, R. B. In *In the Alkaloids*; Manske, R. H. F.; Holmes, H. L., Eds.; Academic Press: New York, 1953; Vol. 3, p 24; Verpoorte, R.; Schripsema, J.; Van der Leer, T. In *In the Alkaloids. Chemistry and Pharmacology*, Brossi, A., Ed.; Academic Press: New York, 1988; Vol. 34; Michael, J. P. In *The Quinoline Alkaloids*, In *Rodd's Chemistry of Carbon Compounds*, 2nd ed.; Sainsbury, M., Ed.; Elsevier: Amsterdam, 1998; 2nd suppl., part F and G, vol 4; 432. They are isolated en masse by extracting the bark of the cinchona tree, which is native to tropical regions. Outside of organic chemistry, the cinchona alkaloids have found wide use as food flavorings (for example as the bitter principle of tonic water) and in the treatment of malaria. Fletcher, D. C. *J. Am. Med. Assoc.* 1976, 236, 305; Mturi, N.; Musumba, C. O.; Wamula, B. M.; Ogutu, B. R.; Newton, C. R. J. C. *CNS Drugs* 2003, 17, 153. Additionally, their roles as ligands, chromatographic selectors, and NMR discriminating agents have been examined extensively over the past thirty years. Several reviews have been published on the catalytic chemistry of cinchona alkaloids over the past four decades. Pracejus, H. *Forschr. Chem. Forsch.* 1967, 8, 493; Morrison, J. D.; Mosher, H. S. *Asymmetric Organic Reactions*; Prentice Hall: Englewood Cliffs, 1971; Wynberg, H. *Top. Stereochem.* 1986, 16, 87; Kacprzak, K.; Gawronski, J. *Synthesis* 2001, 7, 961.

These reactions appear to be broadly applicable to both research and industrial scale asymmetric synthesis of a wide variety of important chiral building blocks, such as hemiesters, α-amino acids and α-hydroxy acids. Commercially available modified dimeric cinchona alkaloids (DHQD)$_2$AQN, (DHQ)$_2$AQN (see FIG. 1), have been identified recently by Deng and coworkers as enantioselective and recyclable catalysts for enantioselective alcoholyses of cyclic anhydrides. However, commercially available (DHQD)$_2$AQN is expensive. For example, the commercial price (Aldrich Chemical Company) for a mole of (DHQD)$_2$AQN is more than $100,000.00. Furthermore, the dimeric catalyst is not available in large quantity (e.g., in kilogram quantity). Therefore, stereoselective reactions using dimeric catalysts are not practical on a relatively large scale (>0.1 mol). Consequently, the development of a new generation of monomeric catalysts that is comparably effective to (DHQD)$_2$AQN, but substantially less costly to produce, is of significant practical value.

Chiral metal and organic catalysts that possess both an acidic and a basic/nucleophilic structural moiety constitute an increasingly powerful platform for the development of asymmetric catalysis. The design and development of such bifunctional chiral catalysts that are efficient yet easily accessible continues to be a major challenge. Wynberg and coworkers demonstrated that natural cinchona alkaloids, via their C9-OH and amine groups, served as bifunctional chiral organic catalysts by activating the nucleophile and electrophile, respectively, for enantioselective reactions. Wynberg, H., Hiemstra, H., *J. Am. Chem. Soc.,* 1981, 103, 417. However, the enantioselectivity of various reactions catalyzed by natural cinchona alkaloids as chiral organic catalysts was usually modest. Hatakeyama and coworkers recently reported a rigid modified cinchona alkaloid that is readily accessible from quinidine. Hatakeyama, S. et al., *J. Am. Chem. Soc.,* 1999, 121, 10219; Hatakeyama, S., *Organic Lett.,* 2003, 5, 3103. The catalyst was found to be efficient for an enantioselective Morita-Baylis-Hillman (MBH) reaction. Both the C6'-OH and the amine groups are believed to be involved in the stabilization of the transition state of the enantioselective MBH reaction.

Remarkably, we have developed readily accessible bifunctional organic catalysts derived from either quinidine or quinine that can be used in highly enantioselective C—C bond forming reactions.

SUMMARY OF THE INVENTION

One aspect of the present invention relates generally to quinine- and quinidine-based catalysts. In certain embodiments, the quinine- and quinidine-based catalysts contain a hydrogen bond donating group at the 6' position. In certain embodiments, the quinine- and quinidine-based catalysts contain a hydroxy group at the 6' position. In certain embodiments, the quinine- and quinidine-based catalysts contain an O-aralkyl group or O-heteroaralkyl group at the C9 position.

Another aspect of the present invention relates to a compound represented by formula I:

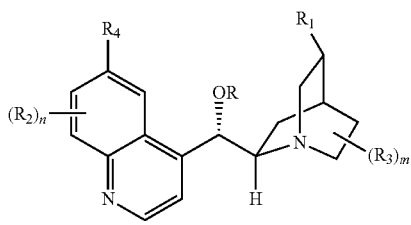

I wherein, independently for each occurrence:

R represents substituted or unsubstituted aralkyl or heteroaralkyl;

$R_1$ represents alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents $OR_5$, wherein $R_5$ is H or alkyl.

Yet another aspect of the present invention relates to a compound represented by formula II:

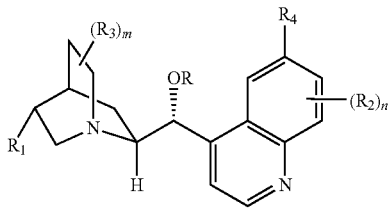

II wherein, independently for each occurrence:

R represents substituted or unsubstituted aralkyl or heteroaralkyl;

$R_1$ represents alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents $OR_5$, wherein $R_5$ is H or alkyl.

The invention also relates to a method of preparing a chiral, non-racemic compound from a prochiral electron-deficient alkene, comprising the step of:

reacting a prochiral electron-deficient alkene with a nucleophile in the presence of a catalyst; thereby producing a chiral, non-racemic compound; wherein said catalyst is represented by formula I or II.

BRIEF DESCRIPTION OF THE DRAWING

FIG. 1 depicts the structure and nomenclature of several cinchona-alkaloid-based catalysts.

DETAILED DESCRIPTION OF THE INVENTION

Definitions

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g., tosylates), chlorides, bromides, iodides, and the like The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The term "Bronsted base" is art-recognized and refers to an uncharged or charged atom or molecule, e.g., an oxide, amine, alkoxide, or carbonate, that is a proton acceptor.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as alkoxides, thiolates, carbanions, and a variety of other organic anions.

The terms "Lewis acid" and "Lewis acidic" are art-recognized and refer to chemical moieties which can accept a pair of electrons from a Lewis base.

The term "meso compound" is recognized in the art and means a chemical compound which has at least two chiral centers but is achiral due to an internal plane, or point, of symmetry.

The term "chiral" refers to molecules which have the property of non-superimposability on their mirror image partner, while the term "achiral" refers to molecules which are superimposable on their mirror image partner. A "prochiral molecule" is an achiral molecule which has the potential to be converted to a chiral molecule in a particular process.

The term "stereoisomers" refers to compounds which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an ee for a particular enantiomer that is larger than the ee of the reaction lacking the chiral catalyst.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant preponderance of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "substrate" is intended to mean a chemical compound which can react with a nucleophile, or with a ring-expansion reagent, according to the present invention, to yield at least one product having a stereogenic center.

The term "catalytic amount" is recognized in the art and means a substoichiometric amount relative to a reactant. As used herein, a catalytic amount means from 0.0001 to 90 mole percent relative to a reactant, more preferably from 0.001 to 50 mole percent, still more preferably from 0.01 to 10 mole percent, and even more preferably from 0.1 to 5 mole percent relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

$$\% \text{ Enantiomeric Excess } A(ee) = (\% \text{ Enantiomer } A) - (\% \text{ Enantiomer } B)$$

where A and B are the enantiomers formed. Additional terms that are used in conjunction with enatioselectivity include "optical purity" or "optical activity". An enantioselective reaction yields a product with an ee greater than zero. Preferred enantioselective reactions yield a product with an ee greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantiomerically-enriched unreacted substrate. Kinetic resolution is usually achieved by the use of sufficient reagent to react with only one reactant enantiomer (i.e., one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another non-identical reactive center. For example, a regioselective reaction of an unsymmetrically substituted epoxide substrate would involve preferential reaction at one of the two epoxide ring carbons.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 of fewer. Likewise, preferred cycloalkyls have from 4-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The terms "alkenyl" and "alkynyl" refer to unsaturated aliphatic groups analogous in length and possible substitution to the alkyls described above, but which contain at least one double or triple carbon-carbon bond, respectively.

As used herein, the term "amino" means $-NH_2$; the term "nitro" means $-NO_2$; the term "halogen" designates $-F$, $-Cl$, $-Br$ or $-I$; the term "thiol" means $-SH$; the term "hydroxyl" means $-OH$; the term "sulfonyl" means —SO$_2$—; and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

The terms "amine" and "amino" are art-recognized and refer to both unsubstituted and substituted amines, e.g., a moiety that can be represented by the general formula:

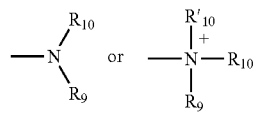

wherein $R_9$, $R_{10}$ and $R'_{10}$ each independently represent a group permitted by the rules of valence.

The term "acylamino" is art-recognized and refers to a moiety that can be represented by the general formula:

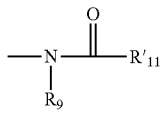

wherein $R_9$ is as defined above, and $R'_{11}$ represents a hydrogen, an alkyl, an alkenyl or —(CH$_2$)$_m$—R$_8$, where m and R$_8$ are as defined above.

The term "amido" is art-recognized as an amino-substituted carbonyl and includes a moiety that can be represented by the general formula:

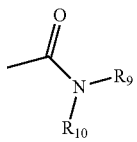

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art-recognized and includes such moieties as can be represented by the general formula:

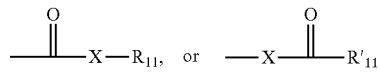

wherein X is a bond or represents an oxygen or a sulfur, and $R_{11}$ represents a hydrogen, an alkyl, an alkenyl, —(CH$_2$)$_m$—R$_8$ or a pharmaceutically acceptable salt, $R'_{11}$ represents a hydrogen, an alkyl, an alkenyl or —(CH$_2$)$_m$—R$_8$, where m and R$_8$ are as defined above. Where X is oxygen and $R_{11}$ or $R'_{11}$ is not hydrogen, the formula represents an "ester". Where X is oxygen, and $R_{11}$ is as defined above, the moiety is referred to herein as a carboxyl group, and particularly when $R_{11}$ is hydrogen, the formula represents a "carboxylic acid". Where X is oxygen, and $R'_{11}$ is hydrogen, the formula represents a "formate". In general, where the oxygen atom of the above formula is replaced by sulfur, the formula represents a "thiolcarbonyl" group. Where X is sulfur and $R_{11}$ or $R'_{11}$ is not hydrogen, the formula represents a "thiolester." Where X is sulfur and $R_{11}$ is hydrogen, the formula represents a "thiolcarboxylic acid." Where X is sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_8$, where m and R$_8$ are described above.

The term "sulfonate" is art-recognized and includes a moiety that can be represented by the general formula:

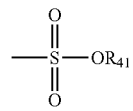

in which $R_{41}$ is an electron pair, hydrogen, alkyl, cycloalkyl, or aryl.

The term "sulfonylamino" is art-recognized and includes a moiety that can be represented by the general formula:

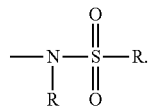

The term "sulfamoyl" is art-recognized and includes a moiety that can be represented by the general formula:

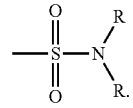

The term "sulfonyl", as used herein, refers to a moiety that can be represented by the general formula:

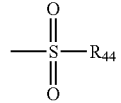

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

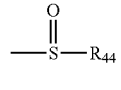

in which $R_{44}$ is selected from the group consisting of hydrogen, alkyl, alkenyl, alkynyl, cycloalkyl, heterocyclyl, aralkyl, or aryl.

The term "sulfate", as used herein, means a sulfonyl group, as defined above, attached to two hydroxy or alkoxy groups. Thus, in a preferred embodiment, a sulfate has the structure:

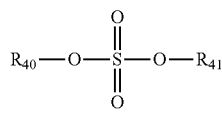

in which $R_{40}$ and $R_{41}$ are independently absent, a hydrogen, an alkyl, or an aryl. Furthermore, $R_{40}$ and $R_{41}$, taken together with the sulfonyl group and the oxygen atoms to which they are attached, may form a ring structure having from 5 to 10 members.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, naphthalene, anthracene, phenanthrene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The term "aralkyl", as used herein, refers to an alkyl group substituted with an aryl group (as defined above). For example, a benzyl group (—$CH_2Ph$) is an aralkyl group.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The term "heteroatom" as used herein means an atom of any element other than carbon or hydrogen. Preferred heteroatoms are nitrogen, oxygen, sulfur, phosphorus and selenium.

For purposes of this invention, the chemical elements are identified in accordance with the Periodic Table of the Elements, CAS version, Handbook of Chemistry and Physics, 67th Ed., 1986-87, inside cover.

The terms ortho, meta and para apply to 1,2-, 1,3- and 1,4-disubstituted benzenes, respectively. For example, the names 1,2-dimethylbenzene and ortho-dimethylbenzene are synonymous.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms, represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, $2^{nd}$* ed.; Wiley: New York, 1991).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

The term "1-adamantyl" is art-recognized and includes a moiety represented by the formula:

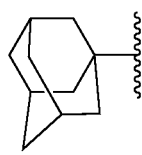 [SMILES: *C12CC3CC(CC(C3)C1)C2]

The term "(−)-menthyl" is art-recognized and includes a moiety represented by the formula:

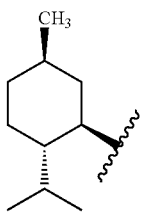 [SMILES: *[C@@H]1C[C@H](C)CC[C@H]1C(C)C]

The term "(+)-menthyl" is art-recognized and includes a moiety represented by the formula:

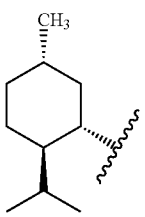 [SMILES: *[C@H]1C[C@@H](C)CC[C@@H]1C(C)C]

The term "isobornyl" is art-recognized and includes a moiety represented by the formula:

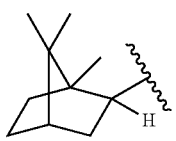 [SMILES: *C1CC2CCC1(C)C2(C)C]

The term "isopinocamphyl" is art-recognized and includes a moiety represented by the formula:

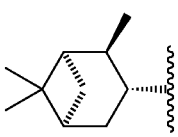

The term "(+)-fenchyl" is art-recognized and includes a moiety represented by the formula:

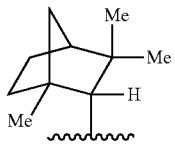

The abbreviation "QD" represents a moiety according to the following formula:

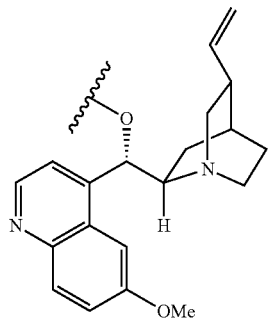 [SMILES: *O[C@@H](c1ccnc2ccc(OC)cc12)C1CC2CCN1CC2C=C]

The term "Q" represents a moiety according to the following formula:

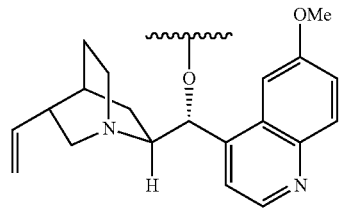 [SMILES: *O[C@H](c1ccnc2ccc(OC)cc12)C1CC2CCN1CC2C=C]

Catalysts of the Invention

The catalysts employed in the subject methods are non-racemic chiral amines which present an asymmetric environment, causing stereochemical discrimination between two stereogenic faces of an alkene; or two or more prochiral moieties (e.g., related by symmetry in a prochiral or meso molecule, (i.e., a molecule comprising at least two chiral centers), both of which comprise an internal plane or point of symmetry or both. In general, catalysts intended by the present invention can be characterized in terms of a number of features. For instance, a salient aspect of each of the catalysts contemplated by the instant invention concerns the use of asymmetric bicyclic or polycyclic scaffolds incorporating the tertiary amine moiety which provide a rigid or semi-rigid environment near the amine nitrogen. This feature, through imposition of structural rigidity on the amine nitrogen in proximity to one or more asymmetric centers present in the scaffold, contributes to the creation of a meaningful difference in the energies of the corresponding diastereomeric transitions states for the overall transformation. Furthermore, the choice of substituents may also effect catalyst reactivity.

As mentioned above, the choice of catalyst substituents can also effect the electronic properties of the catalyst. Substitution of the catalyst with electron-rich (electron-donating) moieties (for example, alkoxy or amino groups) may increase the electron density of the catalyst at the tertiary amine nitrogen, rendering it a stronger nucleophile and/or Bronsted base and/or Lewis base. Conversely, substitution of the catalyst with electron-poor moieties (for example, chloro or trifluoromethyl groups) can result in lower electron density of the catalyst at the tertiary amine nitrogen, rendering it a weaker nucleophile and/or Bronsted base and/or Lewis base. To summarize this consideration, the electron density of the catalyst can be important because the electron density at the tertiary amine nitrogen will influence the Lewis basicity of the nitrogen and its nucleophilicity. Choice of appropriate substituents thus makes possible the "tuning" of the reaction rate and the stereoselectivity of the reaction.

One aspect of the present invention relates to a compound represented by formula I:

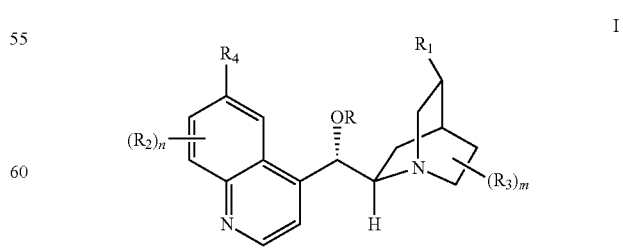

wherein, independently for each occurrence:

R represents substituted or unsubstituted aralkyl or heteroaralkyl;

$R_1$ represents alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents $OR_5$, wherein $R_5$ is H or alkyl.

In certain embodiments, the present invention relates to the aforementioned compound and any of the attendant definitions, wherein $R_5$ is H or $CH_3$.

In certain embodiments, the present invention relates to the aforementioned compound and any of the attendant definitions, wherein $R_5$ is H.

In certain embodiments, the present invention relates to the aforementioned compound and any of the attendant definitions, wherein R represents aralkyl.

In certain embodiments, the present invention relates to the aforementioned compound and any of the attendant definitions, wherein R represents naphthalen-1-yl-methyl.

In certain embodiments, the present invention relates to the aforementioned compound and any of the attendant definitions, wherein R represents anthracene-9-yl-methyl.

In certain embodiments, the present invention relates to the aforementioned compound and any of the attendant definitions, wherein $R_1$ is ethyl.

In certain embodiments, the present invention relates to the aforementioned compound and any of the attendant definitions, wherein $R_1$ is —CH=$CH_2$.

In certain embodiments, the present invention relates to the aforementioned compound and any of the attendant definitions, wherein n is 0.

In certain embodiments, the present invention relates to the aforementioned compound and any of the attendant definitions, wherein m is 0.

In certain embodiments, the present invention relates to the aforementioned compound and any of the attendant definitions, wherein R is aralkyl and $R_1$ is alkyl.

In certain embodiments, the present invention relates to the aforementioned compound and any of the attendant definitions, wherein R is naphthalen-1-yl-methyl, and $R_1$ is ethyl.

In certain embodiments, the present invention relates to the aforementioned compound and any of the attendant definitions, wherein R is anthracene-9-yl-methyl, and $R_1$ is ethyl.

In certain embodiments, the present invention relates to the aforementioned compound and any of the attendant definitions, wherein R is aralkyl and $R_1$ is alkenyl.

In certain embodiments, the present invention relates to the aforementioned compound and any of the attendant definitions, wherein R is naphthalen-1-yl-methyl, and $R_1$ is —CH=$CH_2$.

In certain embodiments, the present invention relates to the aforementioned compound and any of the attendant definitions, wherein R is anthracene-9-yl-methyl, and $R_1$ is —CH=$CH_2$.

In certain embodiments, the present invention relates to the aforementioned compound and any of the attendant definitions, wherein R is aralkyl, $R_1$ is alkyl, m is 0, and n is 0.

In certain embodiments, the present invention relates to the aforementioned compound and any of the attendant definitions, wherein R is naphthalen-1-yl-methyl, $R_1$ is ethyl, m is 0, and n is 0.

In certain embodiments, the present invention relates to the aforementioned compound and any of the attendant definitions, wherein R is anthracene-9-yl-methyl, $R_1$ is ethyl, m is 0, and n is 0.

In certain embodiments, the present invention relates to the aforementioned compound and any of the attendant definitions, wherein R is aralkyl, $R_1$ is alkenyl, m is 0, and n is 0.

In certain embodiments, the present invention relates to the aforementioned compound and any of the attendant definitions, wherein R is naphthalen-1-yl-methyl, $R_1$ is —CH=$CH_2$, m is 0, and n is 0.

In certain embodiments, the present invention relates to the aforementioned compound and any of the attendant definitions, wherein R is anthracene-9-yl-methyl, $R_1$ is —CH=$CH_2$, m is 0, and n is 0.

Another aspect of the present invention relates to a compound represented by formula II:

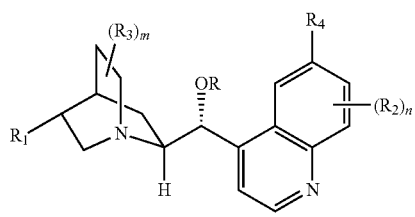

wherein, independently for each occurrence:

R represents substituted or unsubstituted aralkyl or heteroaralkyl;

$R_1$ represents alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents $OR_5$, wherein $R_5$ is H or alkyl.

In certain embodiments, the present invention relates to the aforementioned compound and any of the attendant definitions, wherein $R_5$ is H or $CH_3$.

In certain embodiments, the present invention relates to the aforementioned compound and any of the attendant definitions, wherein $R_5$ is H.

In certain embodiments, the present invention relates to the aforementioned compound and any of the attendant definitions, wherein R represents aralkyl.

In certain embodiments, the present invention relates to the aforementioned compound and any of the attendant definitions, wherein R represents naphthalen-1-yl-methyl.

In certain embodiments, the present invention relates to the aforementioned compound and any of the attendant definitions, wherein R represents anthracene-9-yl-methyl.

In certain embodiments, the present invention relates to the aforementioned compound and any of the attendant definitions, wherein $R_1$ is ethyl.

In certain embodiments, the present invention relates to the aforementioned compound and any of the attendant definitions, wherein $R_1$ is —CH=$CH_2$.

In certain embodiments, the present invention relates to the aforementioned compound and any of the attendant definitions, wherein n is 0.

In certain embodiments, the present invention relates to the aforementioned compound and any of the attendant definitions, wherein m is 0.

In certain embodiments, the present invention relates to the aforementioned compound and any of the attendant definitions, wherein R is aralkyl and $R_1$ is alkyl.

In certain embodiments, the present invention relates to the aforementioned compound and any of the attendant definitions, wherein R is naphthalen-1-yl-methyl, and $R_1$ is ethyl.

In certain embodiments, the present invention relates to the aforementioned compound and any of the attendant definitions, wherein R is anthracene-9-yl-methyl, and $R_1$ is ethyl.

In certain embodiments, the present invention relates to the aforementioned compound and any of the attendant definitions, wherein R is aralkyl and $R_1$ is alkenyl.

In certain embodiments, the present invention relates to the aforementioned compound and any of the attendant definitions, wherein R is naphthalen-1-yl-methyl, and $R_1$ is —CH=CH$_2$.

In certain embodiments, the present invention relates to the aforementioned compound and any of the attendant definitions, wherein R is anthracene-9-yl-methyl, and $R_1$ is —CH=CH$_2$.

In certain embodiments, the present invention relates to the aforementioned compound and any of the attendant definitions, wherein R is aralkyl, $R_1$ is alkyl, m is 0, and n is 0.

In certain embodiments, the present invention relates to the aforementioned compound and any of the attendant definitions, wherein R is naphthalen-1-yl-methyl, $R_1$ is ethyl, m is 0, and n is 0.

In certain embodiments, the present invention relates to the aforementioned compound and any of the attendant definitions, wherein R is anthracene-9-yl-methyl, $R_1$ is ethyl, m is 0, and n is 0.

In certain embodiments, the present invention relates to the aforementioned compound and any of the attendant definitions, wherein R is aralkyl, $R_1$ is alkenyl, m is 0, and n is 0.

In certain embodiments, the present invention relates to the aforementioned compound and any of the attendant definitions, wherein R is naphthalen-1-yl-methyl, $R_1$ is —CH=CH$_2$, m is 0, and n is 0.

In certain embodiments, the present invention relates to the aforementioned compound and any of the attendant definitions, wherein R is anthracene-9-yl-methyl, $R_1$ is —CH=CH$_2$, m is 0, and n is 0.

Methods of the Invention—Catalyzed Reactions

In one aspect of the present invention there is provided a process for stereoselectively producing compounds with at least one stereogenic center from prochiral, or racemic starting materials. An advantage of this invention is that enantiomerically enriched products can be synthesized from prochiral or racemic reactants. Another advantage is that yield losses associated with the production of an undesired enantiomer can be substantially reduced or eliminated altogether.

In general, the invention features a stereoselective conjugate addition process which comprises combining a nucleophilic reactant, a prochiral or chiral substrate, and at least a catalytic amount of non-racemic chiral catalyst of particular characteristics (as described below). The substrate of the reaction will include alkenes susceptible to attack by the nucleophile. The combination is maintained under conditions appropriate for the chiral catalyst to catalyze the conjugate addition between the nucleophilic reactant and alkene substrate. This reaction can be applied to enantioselective processes as well as diastereoselective processes. It may also be adapted for regioselective reactions. Examples of enantioselective reactions, kinetic resolutions, and regioselective reactions which may be catalyzed according to the present invention follow.

The processes of this invention can provide optically active products with very high stereoselectivity (e.g., enantioselectivity or diastereoselectivity) or regioselectivity. In preferred embodiments of the subject desymmetrization reactions, products with enantiomeric excesses of greater than about 50%, greater than about 70%, greater than about 90%, and most preferably greater than about 95% can be obtained. The processes of this invention can also be carried out under reaction conditions suitable for commercial use, and typically proceed at reaction rates suitable for large scale operations.

As is clear from the above discussion, the chiral products produced by the asymmetric synthesis processes of this invention can undergo further reaction(s) to afford desired derivatives thereof. Such permissible derivatization reactions can be carried out in accordance with conventional procedures known in the art. For example, potential derivatization reactions include the Nef reaction, the nucleophilic displacement, the reduction to amino group, the Myer reaction, the conversion into a nitrile oxide, and the like (Scheme 3).

Scheme 3. Various derivatizations of the chiral product of the invention.

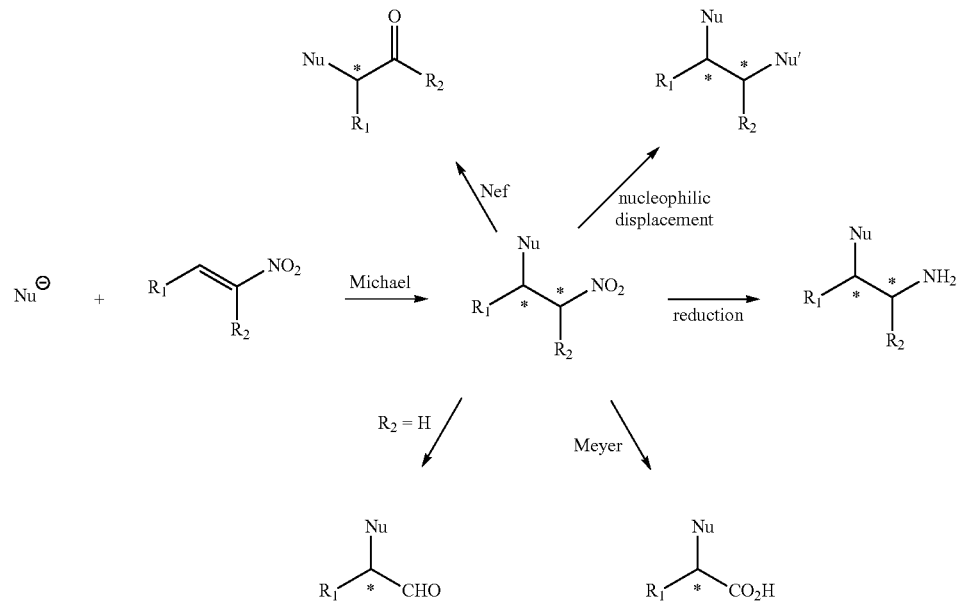

The invention expressly contemplates the preparation of end-products and synthetic intermediates which are useful for the preparation or development or both of therapeutic compounds.

One aspect of the present invention relates to a method of preparing a chiral, non-racemic compound from a prochiral electron-deficient alkene, comprising the step of:

reacting a prochiral electron-deficient alkene with a nucleophile in the presence of a catalyst; thereby producing a chiral, non-racemic compound; wherein said catalyst is represented by formula I:

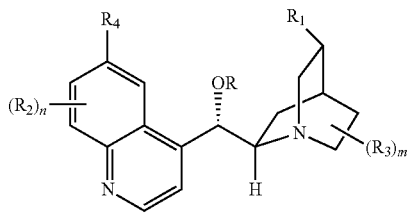

wherein, independently for each occurrence:

R represents substituted or unsubstituted aralkyl or heteroaralkyl;

$R_1$ represents alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents $OR_5$, wherein $R_5$ is H or alkyl.

In certain embodiments, the present invention relates to the aforementioned method and any of the attendant definitions, wherein $R_5$ is H or $CH_3$.

In certain embodiments, the present invention relates to the aforementioned method and any of the attendant definitions, wherein $R_5$ is H.

In certain embodiments, the present invention relates to the aforementioned method and any of the attendant definitions, wherein R represents aralkyl.

In certain embodiments, the present invention relates to the aforementioned method and any of the attendant definitions, wherein R represents naphthalen-1-yl-methyl.

In certain embodiments, the present invention relates to the aforementioned method and any of the attendant definitions, wherein R represents anthracene-9-yl-methyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is —CH=$CH_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is aralkyl and $R_1$ is alkyl.

In certain embodiments, the present invention relates to the aforementioned method and any of the attendant definitions, wherein R is naphthalen-1-yl-methyl, and $R_1$ is ethyl.

In certain embodiments, the present invention relates to the aforementioned method and any of the attendant definitions, wherein R is anthracene-9-yl-methyl, and $R_1$ is ethyl.

In certain embodiments, the present invention relates to the aforementioned method and any of the attendant definitions, wherein R is aralkyl and $R_1$ is alkenyl.

In certain embodiments, the present invention relates to the aforementioned method and any of the attendant definitions, wherein R is naphthalen-1-yl-methyl, and $R_1$ is —CH=$CH_2$.

In certain embodiments, the present invention relates to the aforementioned method and any of the attendant definitions, wherein R is anthracene-9-yl-methyl and $R_1$ is —CH=$CH_2$.

In certain embodiments, the present invention relates to the aforementioned method and any of the attendant definitions, wherein R is aralkyl, $R_1$ is alkyl, m is 0, and n is 0.

In certain embodiments, the present invention relates to the aforementioned method and any of the attendant definitions, wherein R is naphthalen-1-yl-methyl, $R_1$ is ethyl, m is 0, and n is 0.

In certain embodiments, the present invention relates to the aforementioned method and any of the attendant definitions, wherein R is anthracene-9-yl-methyl, $R_1$ is ethyl, m is 0, and n is 0.

In certain embodiments, the present invention relates to the aforementioned method and any of the attendant definitions, wherein R is aralkyl, $R_1$ is alkenyl, m is 0, and n is 0.

In certain embodiments, the present invention relates to the aforementioned method and any of the attendant definitions, wherein R is naphthalen-1-yl-methyl, $R_1$ is —CH=$CH_2$, m is 0, and n is 0.

In certain embodiments, the present invention relates to the aforementioned method and any of the attendant definitions, wherein R is anthracene-9-yl-methyl, $R_1$ is —CH=$CH_2$, m is 0, and n is 0.

In certain embodiments, the present invention relates to the aforementioned method and any of the attendant definitions, wherein said nucleophile is a β-ketoester.

In certain embodiments, the present invention relates to the aforementioned method and any of the attendant definitions, wherein said nucleophile is a alkyl 2-cyano-2-arylacetate.

In certain embodiments, the present invention relates to the aforementioned method and any of the attendant definitions, wherein said prochiral electron-deficient alkene is a nitroalkene.

In certain embodiments, the present invention relates to the aforementioned method and any of the attendant definitions, wherein said prochiral electron-deficient alkene is an alkenyl sulfone.

In certain embodiments, the present invention relates to the aforementioned method and any of the attendant definitions, wherein said prochiral electron-deficient alkene is an alkenyl ketone.

In certain embodiments, the present invention relates to the aforementioned method and any of the attendant definitions, wherein said catalyst is present in less than about 40 mol % relative to said prochiral electron-deficient alkene.

In certain embodiments, the present invention relates to the aforementioned method and any of the attendant definitions, wherein said catalyst is present in less than about 20 mol % relative to said prochiral electron-deficient alkene.

In certain embodiments, the present invention relates to the aforementioned method and any of the attendant definitions, wherein said catalyst is present in less than about 10 mol % relative to said prochiral electron-deficient alkene.

In certain embodiments, the present invention relates to the aforementioned method and any of the attendant definitions, wherein said catalyst is present in less than about 5 mol % relative to said prochiral electron-deficient alkene.

In certain embodiments, the present invention relates to the aforementioned method and any of the attendant definitions, wherein said chrial non-racemic compound has an enantiomeric excess greater than about 70%.

In certain embodiments, the present invention relates to the aforementioned method and any of the attendant definitions, wherein said chrial non-racemic compound has an enantiomeric excess greater than about 90%.

In certain embodiments, the present invention relates to the aforementioned method and any of the attendant definitions, wherein said chrial non-racemic compound has an enantiomeric excess greater than about 95%.

In certain embodiments, the present invention relates to the aforementioned method and any of the attendant definitions, wherein R is aralkyl; R1 is alkyl or alkenyl; and said nucleophile is a β-ketoester.

In certain embodiments, the present invention relates to the aforementioned method and any of the attendant definitions, wherein R is naphthalen-1-yl-methyl; R1 is ethyl; and said nucleophile is a β-ketoester.

In certain embodiments, the present invention relates to the aforementioned method and any of the attendant definitions, wherein R is anthracene-9-yl-methyl; R1 is ethyl; and said nucleophile is a β-ketoester.

In certain embodiments, the present invention relates to the aforementioned method and any of the attendant definitions, wherein R is aralkyl; R1 is alkyl or alkenyl; and said nucleophile is an alkyl 2-cyano-2-aryl acetate.

In certain embodiments, the present invention relates to the aforementioned method and any of the attendant definitions, wherein R is naphthalen-1-yl-methyl; R1 is ethyl; and said nucleophile is an alkyl 2-cyano-2-aryl acetate.

In certain embodiments, the present invention relates to the aforementioned method and any of the attendant definitions, wherein R is anthracene-9-yl-methyl; R1 is ethyl; and said nucleophile is an alkyl 2-cyano-2-aryl acetate.

Another aspect of the present invention relates to a method of preparing a chiral, non-racemic compound from a prochiral electron-deficient alkene, comprising the step of:

reacting a prochiral electron-deficient alkene with a nucleophile in the presence of a catalyst; thereby producing a chiral, non-racemic compound; wherein said catalyst is represented by formula II:

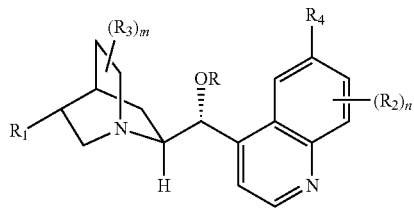

wherein, independently for each occurrence:

R represents substituted or unsubstituted aralkyl or heteroaralkyl;

$R_1$ represents alkyl or alkenyl;

$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

n is an integer from 0 to 5 inclusive;

m is an integer from 0 to 8 inclusive; and $R_4$ represents $OR_5$, wherein $R_5$ is H or alkyl.

In certain embodiments, the present invention relates to the aforementioned method and any of the attendant definitions, wherein $R_5$ is H or $CH_3$.

In certain embodiments, the present invention relates to the aforementioned method and any of the attendant definitions, wherein $R_5$ is H.

In certain embodiments, the present invention relates to the aforementioned method and any of the attendant definitions, wherein R represents aralkyl.

In certain embodiments, the present invention relates to the aforementioned method and any of the attendant definitions, wherein R represents naphthalen-1-yl-methyl.

In certain embodiments, the present invention relates to the aforementioned method and any of the attendant definitions, wherein R represents anthracene-9-yl-methyl.

In certain embodiments, the present invention relates to the aforementioned method and any of the attendant definitions, wherein $R_1$ is ethyl.

In certain embodiments, the present invention relates to the aforementioned method and any of the attendant definitions, wherein $R_1$ is —CH=$CH_2$.

In certain embodiments, the present invention relates to the aforementioned method and any of the attendant definitions, wherein n is 0.

In certain embodiments, the present invention relates to the aforementioned method and any of the attendant definitions, wherein m is 0.

In certain embodiments, the present invention relates to the aforementioned method and any of the attendant definitions, wherein R is aralkyl and $R_1$ is alkyl.

In certain embodiments, the present invention relates to the aforementioned method and any of the attendant definitions, wherein R is naphthalen-1-yl-methyl, and $R_1$ is ethyl.

In certain embodiments, the present invention relates to the aforementioned method and any of the attendant definitions, wherein R is anthracene-9-yl-methyl, and $R_1$ is ethyl.

In certain embodiments, the present invention relates to the aforementioned method and any of the attendant definitions, wherein R is aralkyl and $R_1$ is alkenyl.

In certain embodiments, the present invention relates to the aforementioned method and any of the attendant definitions, wherein R is naphthalen-1-yl-methyl, and $R_1$ is —CH=$CH_2$.

In certain embodiments, the present invention relates to the aforementioned method and any of the attendant definitions, wherein R is anthracene-9-yl-methyl, and $R_1$ is —CH=$CH_2$.

In certain embodiments, the present invention relates to the aforementioned method and any of the attendant definitions, wherein R is aralkyl, $R_1$ is alkyl, m is 0, and n is 0.

In certain embodiments, the present invention relates to the aforementioned method and any of the attendant definitions, wherein R is naphthalen-1-yl-methyl, $R_1$ is ethyl, m is 0, and n is 0.

In certain embodiments, the present invention relates to the aforementioned method and any of the attendant definitions, wherein R is anthracene-9-yl-methyl, $R_1$ is ethyl, m is 0, and n is 0.

In certain embodiments, the present invention relates to the aforementioned method and any of the attendant definitions, wherein R is aralkyl, $R_1$ is alkenyl, m is 0, and n is 0.

In certain embodiments, the present invention relates to the aforementioned method and any of the attendant definitions, wherein R is naphthalen-1-yl-methyl, $R_1$ is —CH=$CH_2$, m is 0, and n is 0.

In certain embodiments, the present invention relates to the aforementioned method and any of the attendant definitions, wherein R is anthracene-9-yl-methyl, $R_1$ is —CH=$CH_2$, m is 0, and n is 0.

In certain embodiments, the present invention relates to the aforementioned method and any of the attendant definitions, wherein said nucleophile is a β-ketoester.

In certain embodiments, the present invention relates to the aforementioned method and any of the attendant definitions, wherein said nucleophile is a alkyl 2-cyano-2-arylacetate.

In certain embodiments, the present invention relates to the aforementioned method and any of the attendant definitions, wherein said prochiral electron-deficient alkene is a nitroalkene.

In certain embodiments, the present invention relates to the aforementioned method and any of the attendant definitions, wherein said prochiral electron-deficient alkene is an alkenyl sulfone.

In certain embodiments, the present invention relates to the aforementioned method and any of the attendant definitions, wherein said prochiral electron-deficient alkene is an alkenyl ketone.

In certain embodiments, the present invention relates to the aforementioned method and any of the attendant definitions, wherein said catalyst is present in less than about 40 mol % relative to said prochiral electron-deficient alkene.

In certain embodiments, the present invention relates to the aforementioned method and any of the attendant definitions, wherein said catalyst is present in less than about 20 mol % relative to said prochiral electron-deficient alkene.

In certain embodiments, the present invention relates to the aforementioned method and any of the attendant definitions, wherein said catalyst is present in less than about 10 mol % relative to said prochiral electron-deficient alkene.

In certain embodiments, the present invention relates to the aforementioned method and any of the attendant definitions, wherein said catalyst is present in less than about 5 mol % relative to said prochiral electron-deficient alkene.

In certain embodiments, the present invention relates to the aforementioned method and any of the attendant definitions, wherein said chrial non-racemic compound has an enantiomeric excess greater than about 70%.

In certain embodiments, the present invention relates to the aforementioned method and any of the attendant definitions, wherein said chrial non-racemic compound has an enantiomeric excess greater than about 90%.

In certain embodiments, the present invention relates to the aforementioned method and any of the attendant definitions, wherein said chrial non-racemic compound has an enantiomeric excess greater than about 95%.

In certain embodiments, the present invention relates to the aforementioned method and any of the attendant definitions, wherein R is aralkyl; R1 is alkyl or alkenyl; and said nucleophile is a β-ketoester.

In certain embodiments, the present invention relates to the aforementioned method and any of the attendant definitions, wherein R is naphthalen-1-yl-methyl; R1 is ethyl; and said nucleophile is a β-ketoester.

In certain embodiments, the present invention relates to the aforementioned method and any of the attendant definitions, wherein R is anthracene-9-yl-methyl; R1 is ethyl; and said nucleophile is a β-ketoester.

In certain embodiments, the present invention relates to the aforementioned method and any of the attendant definitions, wherein R is aralkyl; R1 is alkyl or alkenyl; and said nucleophile is an alkyl 2-cyano-2-aryl acetate.

In certain embodiments, the present invention relates to the aforementioned method and any of the attendant definitions, wherein R is naphthalen-1-yl-methyl; R1 is ethyl; and said nucleophile is an alkyl 2-cyano-2-aryl acetate.

In certain embodiments, the present invention relates to the aforementioned method and any of the attendant definitions, wherein R is anthracene-9-yl-methyl; R1 is ethyl; and said nucleophile is an alkyl 2-cyano-2-aryl acetate.

Nucleophiles

Nucleophiles which are useful in the present invention may be determined by the skilled artisan according to several criteria. In general, a suitable nucleophile will have one or more of the following properties: 1) It will be capable of reaction with the substrate at the desired electrophilic site; 2) It will yield a useful product upon reaction with the substrate; 3) It will not react with the substrate at functionalities other than the desired electrophilic site; 4) It will react with the substrate at least partly through a mechanism catalyzed by the chiral catalyst; 5) It will not substantially undergo further undesired reaction after reacting with the substrate in the desired sense; and 6) It will not substantially react with or degrade the catalyst. It will be understood that while undesirable side reactions (such as catalyst degradation) may occur, the rates of such reactions can be rendered slow—through the selection of reactants and conditions—in comparison with the rate of the desired reaction(s).

Nucleophiles which satisfy the above criteria can be chosen for each substrate and will vary according to the substrate structure and the desired product. Routine experimentation may be necessary to determine the preferred nucleophile for a given transformation. For example, if a nitrogen-containing nucleophile is desired, it may be selected from ammonia, phthalimide, hydrazine, an amine or the like. Similarly, oxygen nucleophiles such as water, hydroxide, alcohols, alkoxides, siloxanes, carboxylates, or peroxides may be used to introduce oxygen; and mercaptans, thiolates, bisulfite, thiocyanate and the like may be used to introduce a sulfur-containing moiety. Additional nucleophiles will be apparent to those of ordinary skill in the art. For nucleophiles which exist as anions, the counterion can be any of a variety of conventional cations, including alkali and alkaline earth metal cations and ammonium cations. In certain embodiments, the nucleophile may be part of the substrate, thus resulting in an intramolecular reaction. The nucleophile may be a primary (eq. 1), secondary (eq. 2), or tertiary (eq. 3) nucleophile as depicted below in Scheme 4.

Scheme 4

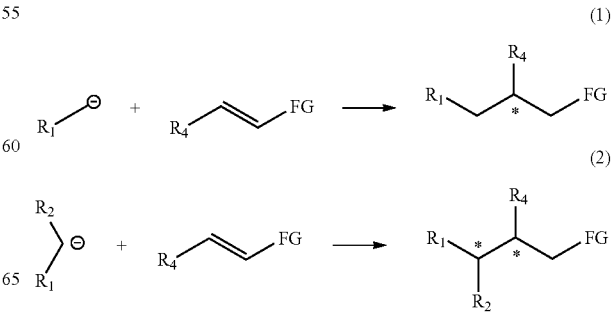

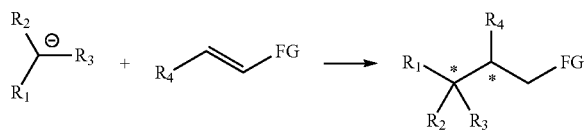

(3)

Substrates

As discussed above, a wide variety of substrates are useful in the methods of the present invention. The choice of substrate will depend on factors such as the nucleophile to be employed and the desired product, and an appropriate substrate will be apparent to the skilled artisan. It will be understood that the substrate preferably will not contain any interfering functionalities. In general, an appropriate substrate will contain at least one reactive electrophilic center or moiety with distinct stereogenic faces; or at least two electrophilic moieties related by an internal plane or point of symmetry at which a nucleophile may attack with the assistance of the catalyst. The catalyzed, stereoselective attack of the nucleophile at the electrophilic center will produce a chiral non-racemic product. Most of the substrates contemplated for use in the methods of the present invention contain at least one double bond. The alkene in some embodiments will comprise an electron withdrawing group making the double bond more susceptible to nucleophilic attack. Examples of suitable alkene substrates which are susceptible to nucleophilic attack by the subject method include nitroalkenes, dialkyl azodicarboxylates, alkenyl sulfones, alkenyl ketones and the like.

In certain embodiments, the alkene is a prochiral or meso compound. In other embodiments, the alkene will be a chiral compound. In certain embodiments, the substrate will be a racemic mixture. In certain embodiments, the substrate will be a mixture of diastereomers. In certain embodiments, the methods of the present invention effect a kinetic resolution. In certain embodiments, the methods of the present invention effect a dynamic kinetic resolution. In certain embodiments, the electron withdrawing group may be a nitro group, a sulfonyl, a ketone, or a carboxylate.

Reaction Conditions

The asymmetric reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely effect the substrate, the catalyst, or the product. For example, the reaction temperature influences the speed of the reaction, as well as the stability of the reactants, products, and catalyst. The reactions will usually be run at temperatures in the range of −78° C. to 100° C., more preferably in the range −20° C. to 50° C. and still more preferably in the range −20° C. to 25° C.

In general, the asymmetric synthesis reactions of the present invention are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments it may be advantageous to employ a solvent which is not inert to the substrate under the conditions employed, e.g., use of ethanol as a solvent when ethanol is the desired nucleophile. In embodiments where water or hydroxide are not preferred nucleophiles, the reactions can be conducted under anhydrous conditions. In certain embodiments, ethereal solvents are preferred. In embodiments where water or hydroxide are preferred nucleophiles, the reactions are run in solvent mixtures comprising an appropriate amount of water and/or hydroxide.

The invention also contemplates reaction in a biphasic mixture of solvents, in an emulsion or suspension, or reaction in a lipid vesicle or bilayer. In certain embodiments, it may be preferred to perform the catalyzed reactions in the solid phase.

In some embodiments, the reaction may be carried out under an atmosphere of a reactive gas. For example, desymmetrization with cyanide as nucleophile may be performed under an atmosphere of HCN gas. The partial pressure of the reactive gas may be from 0.1 to 1000 atmospheres, more preferably from 0.5 to 100 atm, and most preferably from about 1 to about 10 atm.

In certain embodiments it is preferable to perform the reactions under an inert atmosphere of a gas such as nitrogen or argon.

The asymmetric synthesis processes of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral catalyst can be immobilized or incorporated into a polymer or other insoluble matrix by, for example, covalently linking it to the polymer or solid support through one or more of its substituents. An immobilized catalyst may be easily recovered after the reaction, for instance, by filtration or centrifugation.

EXEMPLIFICATION

The invention now being generally described, it will be more readily understood by reference to the following examples which are included merely for purposes of illustration of certain aspects and embodiments of the present invention, and are not intended to limit the invention.

Example 1

Preparation of DHQD-NAPM-OH and DHQD-ANTM-OH Catalysts

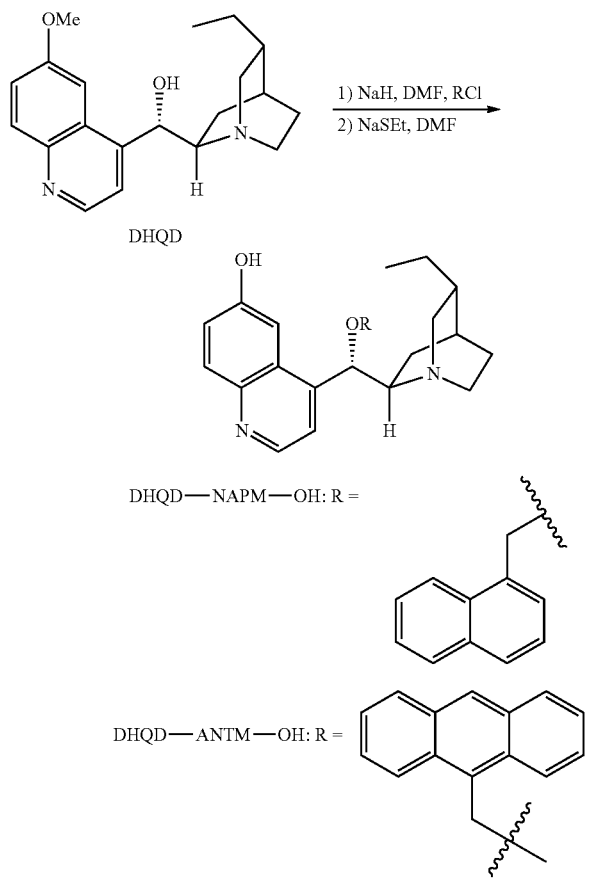

To a solution of dihydroquinidine (4.0 g, 12.4 mmol) in DMF (40 mL) under nitrogen atmosphere, NaH (1.36 g, 57% suspension in mineral oil, 32.3 mmol) was added in small portions and the resulting mixture was stirred at room temperature for 2 h. RCl (13.6 mmol) was added dropwise via a syringe over 10 min. The mixture was stirred at room temperature overnight. After the starting material was completely consumed, brine (40 mL) was added carefully and the resulting mixture was extracted with ethyl acetate (200 mL). The organic phase was washed with $H_2O$ (5×100 mL), brine (100 mL) and dried over $Na_2SO_4$. The solvent was removed in vacuo to afford a light yellow oil. This crude product was used without further purification. Under $N_2$ atmosphere, a suspension of crude product and NaSEt (4.2 g, 50.0 mmol) in dry DMF (75 mL) was stirred at 110° C. for 9 hours. The reaction mixture was cooled to room temperature, and the reaction was quenched with sat. $NH_4Cl$ (80 mL) and $H_2O$ (60 mL). The solution was acidified to pH=2 by addition of conc. HCl. This aqueous solution was washed by ethyl acetate (2×100 mL) and its pH value was adjusted to 8 by conc. ammonium hydroxide. The resulting mixture was extracted with ethyl acetate (2×150 mL). The combined organic phase was dried over $Na_2SO_4$, and concentrated in vacuo to afford a white solid.

NAPM-OH- and ANTM-OH-containing catalysts based on quinidine (QD), quinine (Q) and dihydroquinine (DHQ) may also be prepared in comparable yields using the procedure described in this Example. For example, Q-NAPM-OH may be prepared from Q as the starting material.

Example 2

Evaluation of Improved Catalysts DHQD-NAPM-OH and DHQD-ANTM-OH

The catalysts DHQD-NAPM-OH and DHQD-ANTM-OH were evaluated for their efficiency as catalysts when compared to DHQD-PHN-OH in various conjugate addition reactions.

General Procedure for Conjugate Additions with Various 6'-OH Cinchona Alkaloid Catalysts A Michael donor was added to a solution of the Michael acceptor (14.7 mg, 0.1 mmol) and 10 mol % catalyst in 0.2 mL organic solvent at specified temperature. The reaction was monitored by either $^1H$ NMR (for calculation of reaction conversion) or TLC (for indication of complete reaction). The ee of the products was evaluated by HPLC equipped with a chiral column following literature reported conditions.

When compared to DHQD-PHN-OH, catalysts DHQD-NAPM-OH and DHQD-ANTM-OH showed significant improvement in the rate of the conjugate addition reactions as shown below. Interestingly, the catalysts showed comparable enantioselectivity.

Conjugate Addition of β-Ketoesters to Enones

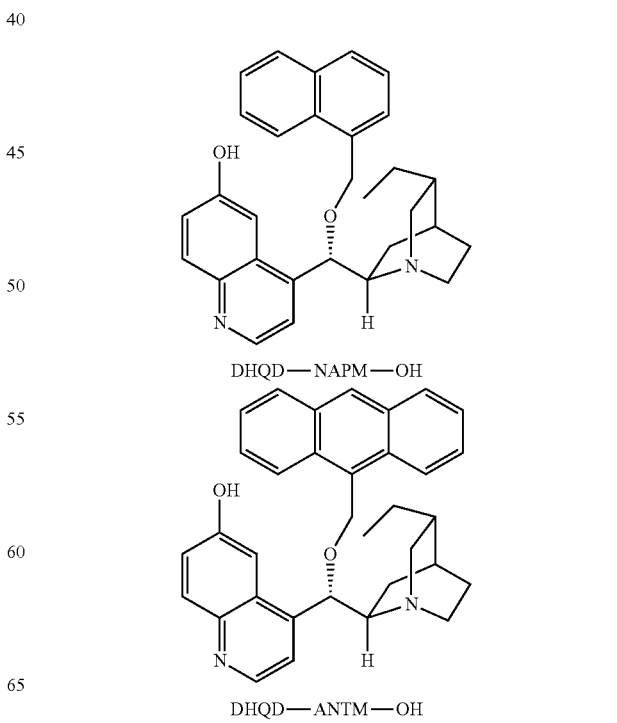

29
-continued

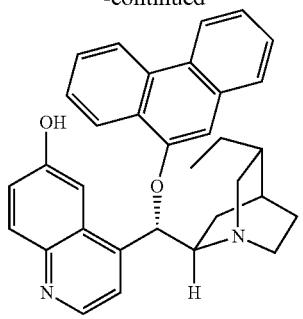

DHQD—PHN—OH

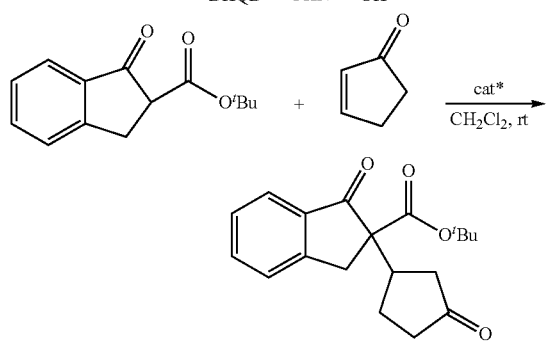

DHQD—NAPM—OH  2 h, 98% yield, 6:1 dr, 96% ee

DHQD—ANTM—OH  2 h, 98% yield, 10:1 dr, 97% ee

DHQD—PHN—OH  12 h, 99% yield, 24:1 dr, 98% ee

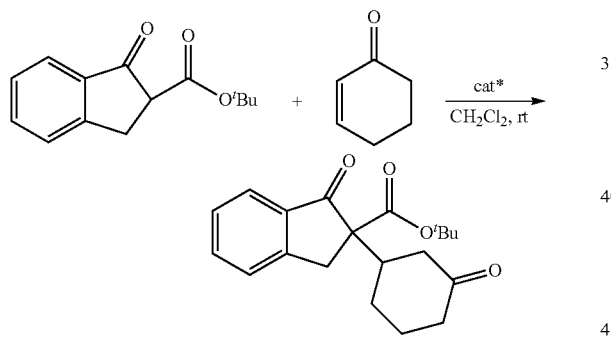

DHQD—NAPM—OH  24 h, 98% yield, 10:1 dr, 86% ee

DHQD—ANTM—OH  24 h, 98% yield, 7:1 dr, 78% ee

DHQD—PHN—OH  120 h, 87% yield, 13:1 dr, 85% ee

Conjugate Addition of α-Cyanoacetates to Nitroolefins

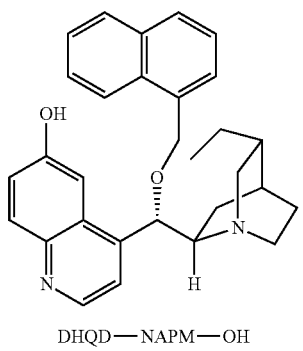

DHQD—NAPM—OH

30
-continued

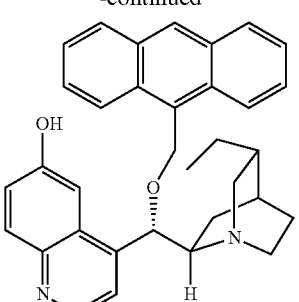

DHQD—ANTM—OH

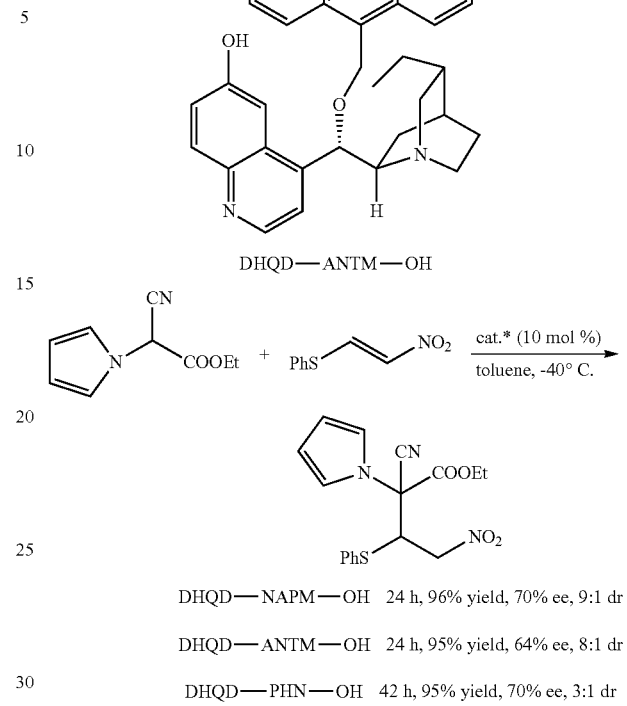

DHQD—NAPM—OH  24 h, 96% yield, 70% ee, 9:1 dr

DHQD—ANTM—OH  24 h, 95% yield, 64% ee, 8:1 dr

DHQD—PHN—OH  42 h, 95% yield, 70% ee, 3:1 dr

Conjugate Additions of α-Cyanoacetates to Vinylsulfones

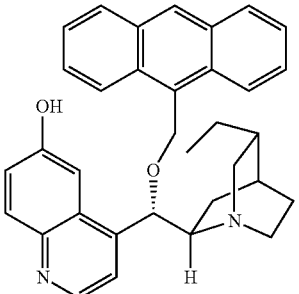

DHQD—ANTM—OH

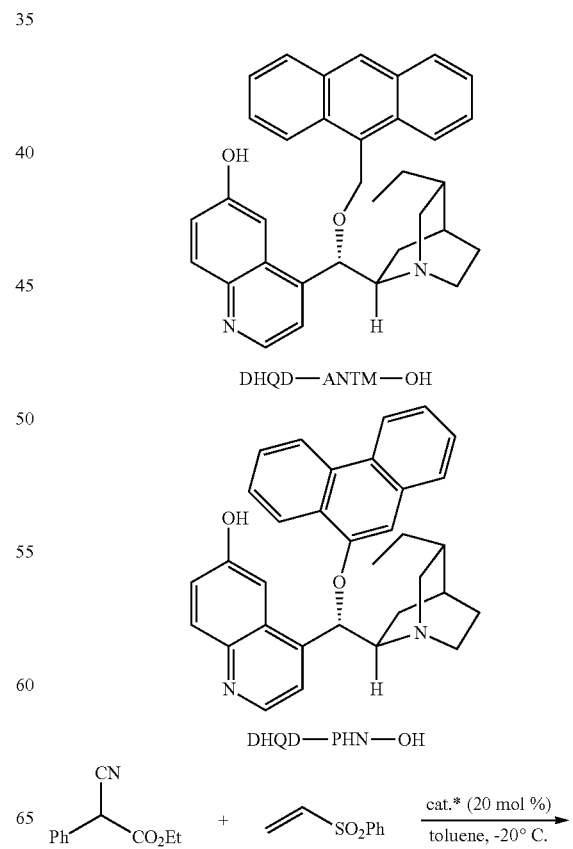

DHQD—PHN—OH

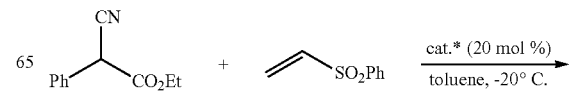

-continued

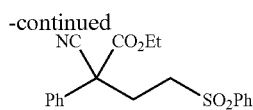

DHQD—ANTM—OH    12 h, 99% yield, 91% ee

DHQD—PHN—OH    72 h, 80% yield, 91% ee

I claim:

1. A compound represented by formula II:

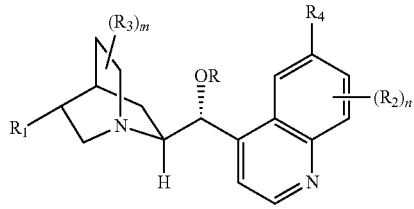

II wherein, independently for each occurrence:
R represents substituted or unsubstituted naphthalen-1-yl-methyl or anthracene-9-yl-methyl;
$R_1$ represents alkyl or alkenyl;
$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;
n is an integer from 0 to 5 inclusive;
m is an integer from 0 to 8 inclusive; and
$R_4$ represents $OR_5$, wherein $R_5$ is H or alkyl.

2. The compound of claim 1, wherein R represents naphthalen-1-yl-methyl.

3. The compound of claim 1, wherein R represents anthracene-9-yl-methyl.

4. The compound of claim 1, wherein $R_5$ is H.

5. The compound of claim 1, wherein R represents naphthalen-1-yl-methyl; and $R_5$ is H.

6. The compound of claim 1, wherein R represents anthracene-9-yl-methyl; and $R_5$ is H.

7. A method of preparing a chiral, non-racemic compound from a prochiral electron-deficient alkene, comprising the step of:

reacting a prochiral electron-deficient alkene with a nucleophile in the presence of a catalyst; thereby producing a chiral, non-racemic compound; wherein said catalyst is represented by formula II:

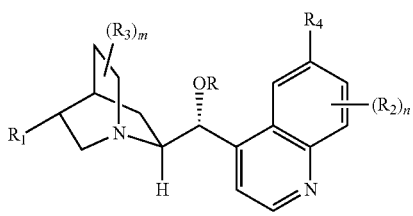

II wherein, independently for each occurrence:
R represents substituted or unsubstituted naphthalen-1-yl-methyl or anthracene-9-yl-methyl;
$R_1$ represents alkyl or alkenyl;
$R_2$ and $R_3$ represent alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;
n is an integer from 0 to 5 inclusive;
m is an integer from 0 to 8 inclusive; and
$R_4$ represents $OR_5$, wherein $R_5$ is H or alkyl.

8. The method of claim 7, wherein said nucleophile is a β-ketoester.

9. The method of claim 7, wherein said nucleophile is a alkyl 2-cyano-2-arylacetate.

10. The method of claim 7, wherein said prochiral electron-deficient alkene is a nitroalkene.

11. The method of claim 7, wherein said prochiral electron-deficient alkene is an alkenyl sulfone.

12. The method of claim 7, wherein said prochiral electron-deficient alkene is an alkenyl ketone.

13. The method of claim 7, wherein R represents naphthalen-1-yl-methyl.

14. The method of claim 7, wherein R represents anthracene-9-yl-methyl.

15. The method of claim 7, wherein $R_5$ is H.

16. The method of claim 7, wherein R represents naphthalen-1-yl-methyl; and $R_5$ is H.

17. The method of claim 7, wherein R represents anthracene-9-yl-methyl; and $R_5$ is H.

* * * * *